US012616719B2

(12) United States Patent
Sekiguchi et al.

(10) Patent No.: US 12,616,719 B2
(45) Date of Patent: May 5, 2026

(54) DISPERSION SOLUTION OF COMPLEX OF CERIUM OXIDE NANOPARTICLE WITH PROTEIN, METHOD OF SCAVENGING REACTIVE SPECIES, AND METHOD OF PRODUCING DISPERSION SOLUTION OF COMPLEX OF CERIUM OXIDE NANOPARTICLE WITH PROTEIN

(71) Applicant: Toray Industries, Inc., Tokyo (JP)

(72) Inventors: Shota Sekiguchi, Kanagawa (JP); Takahiro Motoshiromizu, Kanagawa (JP); Masateru Ito, Kanagawa (JP)

(73) Assignee: Toray Industries, Inc., Tokyo (JP)

( * ) Notice: Subject to any disclaimer, the term of this patent is extended or adjusted under 35 U.S.C. 154(b) by 919 days.

(21) Appl. No.: 17/783,678

(22) PCT Filed: Dec. 25, 2020

(86) PCT No.: PCT/JP2020/048978
§ 371 (c)(1),
(2) Date: Jun. 9, 2022

(87) PCT Pub. No.: WO2021/132659
PCT Pub. Date: Jul. 1, 2021

(65) Prior Publication Data
US 2023/0000906 A1 Jan. 5, 2023

(30) Foreign Application Priority Data

Dec. 26, 2019 (JP) ................................. 2019-236820

(51) Int. Cl.
| | |
|---|---|
| *A61K 33/244* | (2019.01) |
| *A61K 9/10* | (2006.01) |
| *A61K 47/42* | (2017.01) |
| *B82Y 5/00* | (2011.01) |
| *B82Y 30/00* | (2011.01) |

(52) U.S. Cl.
CPC .............. *A61K 33/244* (2019.01); *A61K 9/10* (2013.01); *A61K 47/42* (2013.01); *B82Y 5/00* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 10,722,474 | B2 | 7/2020 | Bell |
| 2010/0242342 | A1* | 9/2010 | Reed ....................... C10L 10/02 44/354 |

FOREIGN PATENT DOCUMENTS

| | | |
|---|---|---|
| JP | 2018-508568 | 3/2018 |
| WO | WO 2017/174437 | * 10/2017 |

OTHER PUBLICATIONS

Bovine Serum Albumin (BSA Protein) 2023.*
Sigma Aldrich-Bovine Serum Albumin (BSA protein) wayback machine 2023.*
Roudbaneh, S.Z.K. et al., "Albumin Binding, Antioxidant and Antibacterial Effects of Cerium Oxide Nanoparticles," *Journal of Molecular Liquids*, 2019, vol. 296, pp. 1-14.
Bhushan, B. et al., "Biomimetic Nanomaterials: Development of Protein Coated Nanoceria as a Potential Antioxidative Nano-Agent for the Effective Scavenging of Reactive Oxygen Species in vitro and in Zebrafish Model," *Colloids and Surfaces B: Biointerfaces*, 2016, vol. 146, pp. 375-386.
Wu, H. et al., "Anionic Cerium Oxide Nanoparticles Protect Plant Photosynthesis from Abiotic Stress by Scavenging Reactive Oxygen Species," *ACS Nano*, 2017, vol. 11, No. 11, pp. 11283-11297.
Patil, S. et al., "Protein Adsorption and Cellular Uptake of Cerium Oxide Nanoparticles as a Function of Zeta Potential," *Biomaterials*, 2007, vol. 28, pp. 4600-4607.
Marsalek, Roman, "Adsorption of Bovine Serum Albumin on $CeO_2$," *Int. J. Bioengineering and Life Sciences*, 2014, vol. 8, No. 12, pp. 1346-1349.
Liu, B. et al., "Boosting the Oxidase Mimicking Activity of Nanoceria by Fluoride Capping: Rivaling Protein Enzymes and Ultrasensitive $F^-$ Detection," *Nanoscale*, 2016, vol. 8, pp. 13562-13567.

* cited by examiner

*Primary Examiner* — Danah Al-Awadi
(74) *Attorney, Agent, or Firm* — DLA Piper LLP (US)

(57) ABSTRACT

A dispersion solution contains a complex of cerium oxide nanoparticle with protein in which a hydrodynamic diameter and zeta potential of the protein are maintained. The dispersion solution is produced by mixing a solution containing the protein with a solution containing a cerium (III) ion or with a cerium (III) salt followed by adding an oxidizing agent thereto.

5 Claims, No Drawings

DISPERSION SOLUTION OF COMPLEX OF CERIUM OXIDE NANOPARTICLE WITH PROTEIN, METHOD OF SCAVENGING REACTIVE SPECIES, AND METHOD OF PRODUCING DISPERSION SOLUTION OF COMPLEX OF CERIUM OXIDE NANOPARTICLE WITH PROTEIN

TECHNICAL FIELD

This disclosure relates to a dispersion solution of a complex of cerium oxide nanoparticle with protein, a method of producing the said dispersion solution, and a method of scavenging reactive species using the dispersion solution.

BACKGROUND

Oxidative stress damages cells in the living body, and it is said that this is related to cardiovascular diseases such as myocardial infarction and cerebral infarction, neurological diseases such as ALS and Parkinson's disease, cancer, inflammation, and aging. Because the causative substances of the oxidative stress are reactive species (reactive oxygen species (ROS) and reactive nitrogen species (RNS)) generated in the living body, an anti-oxidative technology to scavenge these reactive species is considered important in health management and disease prevention. For example, the anti-oxidative technology is used in various ways in our daily lives such as taking vitamin C from foods or applying astaxanthin to skin to protect the skin and cells.

Such anti-oxidative technologies are also expected to be used in medical situations such as applying an antioxidant to a catheter to suppress inflammation or delivering an anti-oxidant to a site of disease through a blood vessel. Therefore, it is necessary to improve the biocompatibility and retentivity in blood. If the protein, which is abundant in the body, can be provided with an anti-oxidative property, it is expected that this can be used as an antioxidant having high biocompatibility and retentivity in blood.

One possible way to provide a protein with an anti-oxidative property is to complex it with an antioxidant such as a vitamin, but such an antioxidant is generally active in a consumable form, so this does not have a durable effect. Therefore, it is desirable to complex it with a material having a durable anti-oxidative property.

On the other hand, a cerium oxide nanoparticle (nanoceria) has an anti-oxidative property. It is known that this has a catalytic activity similar to such enzymes as a catalase and a superoxide dismutase. It is also reported that this, due to the antioxidative property thereof, is related to the therapeutic effect against Parkinson's disease, to reduction in the damage from an ischemic disease that occurs during cerebral infarction, and to improvement in the sperm motility. Because cerium oxide is a ceramic, it is chemically stable and has a durable anti-oxidative property. Therefore, if a protein can be complexed with a cerium oxide nanoparticle, it is expected that the protein can be provided with a durable anti-oxidative property.

In this context, Swanand Patil, et al., "Protein Adsorption and Cellular Uptake of Cerium Oxide Nanoparticles as a Function of Zeta Potential," Biomaterials 2007, 28, 4600-4607 and Roman Marsalek, "Adsorption of Bovine Serum Albumin on $CeO_2$" Int. J. Bioeng. and Life Sci. 2014, 8, 1346-1349 disclose that when the nanoceria is mixed with BSA, which is a protein, the BSA is adsorbed onto the surface of nanoceria, and the adsorption amount thereof varies depending on the pH of the solution or on the electric potential of the nanoceria.

Also, FIG. 4C of Biwu Liu, et al., "Boosting the Oxidase Mimicking Activity of Nanoceria by Fluoride Capping: Rivaling Protein Enzymes and Ultrasensitive $F^-$ Detection," Nanoscale 2016, 8, 13562-13567 discloses that the enzymatic activity of the nanoceria is decreased when the nanoceria is mixed with BSA.

With the aim to obtain an antioxidant having high biocompatibility and retentivity in the blood, we studied obtaining a dispersion solution having a cerium oxide nanoparticle complexed with protein, wherein the solution has an anti-oxidative property. However, as described in Comparative Examples later, when the methods described in Patil, et al. and Marsalek were applied, aggregation of the complex occurred, thereby leading to a significant increase in the hydrodynamic diameter thereof. Under other conditions, aggregation could be suppressed, but the electrostatic properties of the complex as indicated by the zeta potential deviated significantly from those of the protein. As a result, in the complexes obtained by the methods described in Patil, et al. and Marsalek, there occurred the problems of the loss of the biocompatibility and the retentivity in the blood, which are the properties characteristic of the protein.

It therefore became apparent that it could be helpful to provide a dispersion solution of a complex of cerium oxide nanoparticle with protein while the hydrodynamic diameter and zeta potential of the protein are maintained.

SUMMARY

We studied ways to complex the cerium oxide nanoparticle with the protein. As a result, we found that by mixing a solution containing a protein with a solution containing a cerium (III) ion or with a cerium (III) salt followed by adding an oxidizing agent, thereby producing a complex, the cerium oxide nanoparticle and the protein can be complexed while the hydrodynamic diameter and zeta potential of the protein are maintained.

We thus provide:

(1) A dispersion solution of a complex of cerium oxide nanoparticle with protein, the dispersion solution being produced by mixing a solution containing the protein with a solution containing a cerium (III) ion or with a cerium (III) salt followed by adding an oxidizing agent thereto.

(2) The dispersion solution of the complex of cerium oxide nanoparticle with protein according to (1), wherein a molecular weight of the protein is in a range of 5 kD to 200 kD both inclusive.

(3) The dispersion solution of the complex of cerium oxide nanoparticle with protein according to (1) or (2), wherein the protein is a protein present in blood.

(4) The dispersion solution of the complex of cerium oxide nanoparticle with protein according to any one of (1) to (3), wherein the protein is albumin or globulin.

(5) The dispersion solution of the complex of cerium oxide nanoparticle with protein according to any one of (1) to (4), wherein a hydrodynamic diameter of the dispersion solution is 10 times or less compared to a hydrodynamic diameter indicated by a solution containing the protein.

(6) The dispersion solution of the complex of cerium oxide nanoparticle with protein according to any one of (1) to (5), wherein a zeta potential thereof at pH 7 is −15 mV to +15 mV compared to a zeta potential indicated by a solution containing the protein at pH 7.

(7) A method for scavenging reactive species, the method comprising bringing a sample including the reactive species in contact with the dispersion solution of the complex of cerium oxide nanoparticle with protein according to any one of (1) to (6).

(8) A method for producing a dispersion solution of a complex of cerium oxide nanoparticle with protein, the method comprising: mixing a solution containing the protein with a solution containing a cerium (III) ion or with a cerium (III) salt; and adding an oxidizing agent thereto.

Our dispersion solution can be used as the antioxidant having a high biocompatibility.

DETAILED DESCRIPTION

The dispersion solution of the complex of cerium oxide nanoparticle with protein is sometimes described as the dispersion solution.

The term protein is a generic term for high molecular weight compounds in which L-a-amino acids (including glycine) are linked by the peptide bond, thereby having a molecular weight of 5 kD or more. The protein includes a natural protein extracted and purified from a natural product, a recombinant protein expressed from microorganisms such as *Escherichia coli*, a synthetic protein obtained by peptide synthesis or chemical ligation, and a semi-synthetic protein having a polypeptide attached to a natural protein by a ligation reaction. This may also have a sugar chain, a lipid, a phosphate group or the like, which are added during post-translational modification, or this may form a multimer as well. Also, a part thereof may be displaced with an artificial amino acid.

The protein is preferably present in the blood, because biocompatibility and retentivity in the blood are required.

Preferable examples of the protein are albumin and globulin.

The lower limit of the molecular weight of the protein is preferably 5 kD or more, while more preferably 10 kD or more. The upper limit thereof is preferably 200 kD or less, while more preferably 180 kD or less. The molecular weight is preferably 5 kD to 200 kD, while more preferably 10 kD to 180 kD.

The dispersion solution includes a complex of a cerium oxide nanoparticle composed of a mixture of $Ce_2O_3$ and $CeO_2$ with the protein described above. As for the affinity in the complex formation, it is presumed that a hydrophobic interaction, a hydrogen bond, an electrostatic interaction, a metal chelate, or a combination of them is involved between the cerium oxide and the protein. This disclosure is not limited to any of these interactions.

The cerium oxide nanoparticle may be covered with a polymer such as polyacrylic acid having a carboxylic acid group or a dextran having a hydroxyl group to obtain dispersibility into a solvent. A protein has in its side chain and terminal of amino acids many functional groups possessed by these polymers. Thus, it is presumed that the complex with the cerium oxide is formed by the combination of these functional groups. The complex of the cerium oxide nanoparticle with the protein having the molecular weight in the above-mentioned range can acquire a sufficient dispersibility in a solvent.

In addition to the complex and water as a dispersant, the dispersion solution may include other solvent components that are soluble in water. Illustrative examples of the other solvent component include methanol, ethanol, propanol, isopropanol (2-propanol), butanol, tert-butanol, acetone, dimethylformamide (DMF), dimethyl sulfoxide (DMSO), glycerol, ethyleneglycol, and oligoethyleneglycol. These solvent components may be included to be 50% or less by volume.

The dispersion solution may include an ionic component. The ionic component may be, as the component that imparts a buffering property, acetic acid, phthalic acid, succinic acid, carbonic acid, tris(hydroxymethyl)aminomethane (Tris), 2-morpholinoethanesulfonic acid monohydrate (MES), bis (2-hydroxyethyl)iminotris(hydroxymethyl)methane (Bis-Tris), N-(2-acetamido)iminodiacetic acid (ADA), piperazine-1,4-bis(2-ethanesulfonic acid) (PIPES), N-(2-acetamido)-2-aminoethanesulfonic acid (ACES), 2-hydroxy-3-morpholinopropanesulfonic acid (MOPSO), N,N-bis(2-hydroxyethyl)-2-aminoethanesulfonic acid (BES), 3-morpholinopropanesulfonic acid (MOPS), N-tris (hydroxymethyl)methyl-2-aminoethanesulfonic acid (TES), 2-[4-(2-hydroxyethyl)-1-piperazinyl]ethanesulfonic acid (HEPES), 2-hydroxy-N-tris(hydroxymethyl)methyl-3-aminopropanesulfonic (TAPSO), piperazine-1,4-bis(2-hydroxy-3-propanesulfonic acid) (POPSO), 2-hydroxy-3-[4-(2-hydroxyethyl)-1-piperazinyl]propanesulfonic acid (HEPSO), 3-[4-(2-hydroxyethyl)-1-piperazinyl]propanesulfonic acid (HEPPS), (Tricine), N,N-bis(2-hydroxyethyl)glycine (Bicine), and N-tris(hydroxymethyl)methyl-3-aminopropanesulfonic acid (TAPS). As for the component that does not impart a buffering property, sodium chloride and potassium chloride may be mentioned.

The pH of the dispersion solution may be 2 to 12, preferably 4 to 10, while more preferably 5 to 8. The pH may be adjusted by adding a buffer solution, an acid such as nitric acid, sulfuric acid, or hydrochloric acid, or a base such as sodium hydroxide or potassium hydroxide.

The hydrodynamic diameter of the complex of cerium nanoparticle with protein in the dispersion solution is calculated as the average particle diameter by measuring the dynamic light scattering of the complex to obtain the autocorrelation function followed by analyzing this with the Marquadt method, thereby calculating the diameter from the number conversion histogram. Measurement of the dynamic light scattering is done by using ELS-Z manufactured by Otsuka Electronics Co., Ltd. The hydrodynamic diameter of the complex in the dispersion solution may be 10 times or less, while preferably 5 times or less, as compared to the hydrodynamic diameter of the solution containing the protein.

The zeta potential is one of the values that describe the electrical properties of the colloidal interface in a solvent. When a charged colloid is dispersed in a solvent, an electric double layer is formed on the surface of the colloid by a counterion to the surface charge of the colloid. The potential of the colloidal surface is called the surface potential. Because the electric double layer is formed by the electrostatic interaction of the colloidal surface charges, the nearer the colloid the ions are, the more strongly the ions are fixed. In the electric double layers, the layer in which the counterions are strongly fixed to the colloidal surface by the electrostatic interaction is called the fixed layer, and the potential of the fixed layer is called the fixed potential. When the colloid is moved against the solvent, the fixed layer moves with the colloid. At this time, there is a boundary surface outside the fixed layer seen from the colloid, in which the boundary moves with the colloid due to the viscosity of the solvent. This is called a slipping plane. When the potential at a point far enough away from the colloid is set to zero, the potential of this sliding surface is defined as the zeta potential. Thus, the zeta potential changes depending on the surface charge of the colloid; and because the surface charge changes due to the pH-dependent proton attachment and detachment, the zeta potential is based on the value in the solution at pH 7 as the standard. Because the distance between the sliding surface and the colloidal surface is generally smaller compared to the size of the colloid, the colloidal surface may be approximated by the sliding surface. Similarly, in our dispersion solution, the surface potential of the colloid dispersed in the solvent can be regarded as the zeta potential.

The zeta potential can be obtained using interfacial electrokinetic phenomena such as an electrophoresis, an electroosmosis, a backflow potential, and a precipitation potential. Thus, this can be measured by the method such as a microscopic electrophoresis method, an electrophoresis method using a rotating diffraction grating method, a laser Doppler electrophoresis method, an ultrasonic vibration potential method, and an electrokinetic acoustic method. These kinds of measurement may be done by using a zeta potential measurement instrument. The zeta potential measurement instrument is commercially available from Otsuka Electronics Co., Ltd., Malvern Instruments Ltd, Ranku Brothers Ltd, PenKem Inc. and the like.

Any of the above instruments may be used to measure the zeta potential, but the laser Doppler electrophoresis method is generally used. The laser Doppler electrophoresis method is the measurement method that utilizes the Doppler effect, in which when a light or a sound wave hits an object in motion by electrophoresis, the frequency thereof changes upon scattering or reflection.

When measuring the zeta potential of the dispersion solution, the dispersion solution can be measured as a colloidal dispersion solution. Before the measurement, for example, the dispersion solution may be diluted with water, or added with an electrolyte such as a HEPES buffer solution or a sodium chloride solution. The measurement is conducted by detecting the scattered light or the reflected light of the complex of cerium oxide nanoparticle with protein included in the dispersion solution. When the size of the complex of cerium oxide nanoparticle with protein is larger, the scattered light or the reflected light can be detected with a lower concentration thereof.

The specific conditions for measurement of the zeta potential of the dispersion solution by the laser Doppler method are not particularly limited. For example, the complex of cerium oxide nanoparticle with protein is dispersed in the HEPES buffer solution (50 mM, pH 7) such that the concentration thereof may become 0.1 to 10 mg/mL. Then, the dispersion solution thus obtained is poured into a measurement cell followed by placing this in the zeta potential measurement instrument based on the principle of the laser Doppler electrophoresis method to measure the zeta potential at room temperature. As for the zeta potential measurement instrument, for example, ELS-Z manufactured by Otsuka Electronics Co., Ltd. may be used.

The zeta potential indicated by the dispersion solution may be −15 mV to +15 mV, while preferably −10 mV to +10 mV compared to the zeta potential of the solution containing the protein at pH 7.

The dispersion solution may be produced by mixing a solution containing the protein with a solution containing a cerium (III) ion or with a cerium (III) salt followed by adding an oxidizing agent thereto. Hereinafter, each process of the method of producing the dispersion solution will be separately described.

The protein solution may be prepared by dissolving the above-described protein into an arbitrary solvent. The solvent is preferably water or a solvent that is soluble in water is preferable. Specifically, illustrative examples of the water-soluble solvent include methanol, ethanol, propanol, isopropanol (2-propanol), butanol, tert-butanol, acetone, dimethylformamide (DMF), dimethyl sulfoxide (DMSO), glycerol, ethyleneglycol, and oligoethyleneglycol. These solvent components may be included to be 50% or less by volume. When the protein is difficult to be dissolved, this may be dissolved by heating or sonication, or a salt such as sodium chloride or potassium chloride may be added to adjust the salt strength. The concentration of the protein solution is preferably 0.1 mg/mL to 10 mg/mL.

Mixing of the protein solution with the solution including the cerium (III) ion or with the cerium (III) salt may be conducted by mixing the protein solution with the solution including the cerium (III) ion after these solutions were separately prepared in advance. Alternatively, when the solvent of the protein solution is water or a water-soluble solvent, the cerium (III) salt may be added into the protein solution for mixing. The solution including the cerium (III) ion may be prepared by dissolving the cerium (III) salt into an arbitrary solvent. Illustrative examples of the cerium (III) salt include cerium (III) nitrate hexahydrate.

When the cerium (III) nitrate hexahydrate is used as the cerium (III) salt, the mass ratio of the cerium (III) nitrate hexahydrate to the protein may be 0.1 to 100 both inclusive, while this is preferably 0.5 to 50. The resulting mixture solution is preferably mixed for 5 minutes or longer until the solution becomes homogeneous.

Illustrative examples of the oxidizing agent to be added after the protein solution is mixed with the solution including the cerium (III) ion or with the cerium (III) salt include nitric acid, potassium nitrate, hypochlorous acid, chlorous acid, chloric acid, perchloric acid, halogens, hydrogen halides, permanganate salts, chromic acid, dichromic acid, oxalic acid, hydrogen sulfide, sulfur dioxide, sodium thiosulfate, sulfuric acid, and hydrogen peroxide. Among these, hydrogen peroxide is especially preferable. The addition amount thereof relative to the cerium (III) ion as the molar equivalent may be 0.1 to 10 equivalents, while this is preferably 0.5 to 2 equivalents.

When the oxidizing agent is added after the protein solution is mixed with the solution containing the cerium (III) ion or with the cerium (III) salt, the cerium (III) ion is oxidized to cerium (IV), resulting in formation of the cerium oxide particle consisting of a mixture of $Ce_2O_3$ and $CeO_2$; then, the reaction to form the complex of cerium oxide nanoparticle with protein is started. During this reaction, the solution is colored in yellow, orange, red, brown or the like. This coloring takes place because the cerium (III) ion changes to cerium (IV) in which the coloring degree is determined by the ratio of cerium (III) to cerium (IV) that are present on the surface of the cerium oxide nanoparticle. Termination of the reaction can be judged at the time when the color does not change any further. The particle formation reaction depends on pH, in which the reaction proceeds in a weakly acidic to a basic solution. The pH moves to the acidic side as the reaction progresses. So, during the time from addition of the oxidant until the end of the reaction, it is preferable to keep the reaction solution at pH 5 or higher, more preferably at pH 6 or higher, while still more preferably at pH 7 or higher. To adjust the pH, a sodium hydroxide aqueous solution or an ammonia aqueous solution may be used. During the reaction, the solution may be heated or cooled. It is preferable to carry out the reaction in the temperature range where the solution is homogeneous because the protein may denature and aggregate, causing the solution to become cloudy. The reaction usually terminates in about 30 minutes to 1 hour.

The dispersion solution may be stored as the reaction solution after completion of the reaction to form the complex, or this may be purified after completion of the reaction and then stored. At the time of storage, refrigeration is preferable, or this may also be stored by freezing with the addition of glycerol or the like. When the dispersion solution is purified, the unreacted oxidizing agent and the cerium (III) ion that remain in the dispersion solution after completion of the reaction may be removed by filtrating the dispersion solution after completion of the reaction by an ultrafiltration membrane or by dialyzing by a semi-permeative membrane.

The dispersion solution may be sterilized prior to use. The sterilization may be conducted by the method in which the dispersion solution is passed through a sterile filter.

The dispersion solution can be used to scavenge the reactive species included in the sample. To scavenge the reactive species means to eliminate the reactivity thereof so as to become harmless to a living body. The reactive species that can be scavenged by the dispersion solution may be reactive oxygen species (ROS) and reactive nitrogen species (RNS) that are present in a living body. Specifically, illustrative examples thereof include a superoxide anion ($\cdot O_2^-$), a hydroxyl radical (HO$\cdot$), a hydroperoxyl radical (HOO$\cdot$), a singlet oxygen ($^1O_2$), hydrogen peroxide ($H_2O_2$), nitrogen monooxide (NO), a peroxynitrite anion (ONOO$\cdot$), and a nitrogen dioxide radical ($\cdot NO_2$). Detoxification refers, for example, to decomposition of hydrogen peroxide, which is one of the reactive species, into water and oxygen, transformation of the superoxide anion ($\cdot O_2^-$) into a molecular oxygen, and transformation of the hydroxyl radical (HO$\cdot$) into a hydroxide ion. At the time of scavenging, an arbitrary sample that includes these reactive species may be used. These performances may be evaluated by the catalase activity, which will be described below.

The value of the catalase activity may be obtained in accordance with the protocol by using AmplexRed Catalase Assay Kit (A22180), manufactured by Thermo Fisher Scientific Inc., as described in Japanese Translation of PCT International Application No. 2018-508568. The Reaction Buffer included in the kit, the dispersion solution, and the aqueous hydrogen peroxide solution are mixed. Then, the resulting mixture is allowed to statically leave for 30 minutes to carry out the decomposition reaction of hydrogen peroxide. The reaction solution is passed through a 30 kD ultrafiltration membrane. Then, the flow-through solution is mixed with Working Solution included in the kit to carry out the reaction at 37° C. for 30 minutes. The resorufin generated by the reaction is excited at 544 nm, and the fluorescence intensity at 590 nm is measured. By comparing with the calibration curve of the catalase standard that is included in the kit, the activity value thereof being known, the catalase activity of the dispersion solution is calculated. For measurement of the catalase activity, other kits such as EnzyChrom Catalase Assay Kit manufactured by BioAssay Systems, LLC may also be used.

When the dispersion solution is used to scavenge the reactive species, the dispersion solution after completion of the formation reaction of the above-mentioned complex may be brought into contact, as it is, with the sample including the reactive species, or the dispersion solution having been purified as described above may be brought into contact with the sample. As for the method to contact, when the sample including the reactive species is a liquid, the dispersion solution of the present invention may be added to and mixed with the sample, or the dispersion solution may be sprayed in the atomized form. When the sample is a solid, the dispersion solution may be added to, and whereby contacting with the sample. Alternatively, the dispersion solution is added to a textile, a tube, a bead, a rubber, a film, a plastic material or the like during molding, or is applied onto the surface of these materials. Then, this may be brought into contact with the sample that includes the reactive species.

Furthermore, the dispersion solution may be used as an antioxidant in a drug to treat an oxidation stress or an inflammation of a human or of an animal. Specifically, the dispersion solution may be administered to a subject by injection or drip infusion. This may also be atomized as an aerosol so that this can be administered to a subject through the respiratory tract using an inhaler. In addition, this may be processed into a cream, a lotion, and an ointment by using, as the base substrate, an ingredient such as a fat, a fatty oil, lanolin, Vaseline, a paraffin, a wax, a resin, a plastic material, a glycol, a higher alcohol, glycerin, water, an emulsifier, or a suspending agent; and then, this may be administered to a subject through a skin. This may also be combined with an excipient and processed into a gel, a tablet, an enteric-coated tablet, powder, a suppository, or a lozenge for oral or enteral administration to a subject. By administering with the method as described above, this may be used for prevention and treatment of the disease that relates to the oxidation stress such as apoplectic stroke, disseminated sclerosis, amyotrophic lateral sclerosis, and ischemia reperfusion damage.

Also, the dispersion solution may be used to reduce inflammation topically or systemically by coating this as the antioxidant on the surface of an artificial organ represented by a dialysis membrane and medicinal equipment such as a cannula, a catheter, and a stent.

The dispersion solution may be used for protection of a skin and cells as the antioxidant. Specifically, this may be administered to the skin in the manner described above, added to a cell culture medium, or applied to a culture vessel such as a Petri dish.

The dispersion solution may be used as an alternative to a conventional antioxidative enzyme solution. Specifically, as a substitute of a catalase solution, this may be used in a detection reaction of hydrogen peroxide or in an electrochemical detection reaction by coating the dispersion solution to an electrode to immobilize the cerium oxide nanoparticle. In addition, this may be used as a neutralizing solution of hydrogen peroxide used in an industry such as foods, semiconductor, textile, pulp and paper manufacturing, as well as for sterilization of a public bath and to remove slime in a piping.

In addition, the dispersion solution may be added to an oil, a detergent, foods, and an animal feed as the antioxidant.

A suitable example of the dispersion solution is: the dispersion solution of the complex of protein with cerium oxide nanoparticle in which the hydrodynamic diameter thereof is 10 times or less as compared to the hydrodynamic diameter indicated by the solution containing the protein, and the dispersion solution of the complex of cerium oxide nanoparticle with protein in which the zeta potential at pH 7 is in the range of −15 mV to +15 mV compared to the zeta potential indicated by the solution containing the protein at pH 7.

A suitable example of the dispersion solution is also the dispersion solution of the complex of protein with cerium oxide nanoparticle in which the catalase activity in the decomposition reaction of a hydrogen peroxide aqueous solution is 1.0 U/mL or higher, using the AmplexRed Catalase Assay Kit (A22180) manufactured by Thermo Fisher Scientific Inc. and measured with the cerium oxide nanoparticle concentration of 100 μg/mL. When the catalase activity in the decomposition reaction of the hydrogen peroxide aqueous solution using the AmplexRed Catalase Assay Kit (A22180) is 1.0 U/mL or higher, this can be used as the antioxidant. The catalase activity of 1.2 U/mL or higher is especially preferable.

EXAMPLES

Our dispersion solutions, methods and kits will be explained more specifically by the following Examples.

Materials and Methods

Bovine serum albumin (BSA), ovalbumin (OVA), human serum-derived immunoglobulin (IgG), and the commercially available nanoceria dispersion solution (particle diameter <5 nm) used in Comparative Examples were obtained from Merck, and cerium (III) nitrate hexahydrate and 30% by mass of aqueous hydrogen peroxide solution were obtained from FUJIFILM Wako Pure Chemicals Corporation.

Other reagents were purchased from FUJIFILM Wako Pure Chemical Corporation, Tokyo Chemical Industry Co., Ltd., and Sigma-Aldrich Co., LLC. They were used as they were without any further purification.

The catalase activity was measured by using AmplexRed Catalase Assay Kit (A22180) manufactured by Thermo Fisher Scientific Inc.

For measurement of the hydrodynamic diameter of the complex of cerium oxide nanoparticle with protein, the zeta potential and particle measurement system ELS-Z of Otsuka Electronics Co., Ltd was used.

Reference Example 1

Measurement of Hydrodynamic Diameter and Zeta Potential of Commercially Available Aqueous Nanoceria Solution, BSA Aqueous Solution, and OVA Aqueous Solution A commercially available aqueous nanoceria solution was diluted into 25-mM HEPES buffer solution (pH 7), and then, the hydrodynamic diameter and zeta potential thereof were measured. BSA and OVA each were dissolved in 25-mM HEPES buffer solution (pH 7), and then, the hydrodynamic diameter and zeta potential thereof were measured. The results are listed in Table 1.

TABLE 1

| Sample | Hydrodynamic diameter [nm] | Zeta potential [mV] |
|---|---|---|
| Commercially available nanoceria aqueous solution | 2.7 ± 0.7 | +27.83 |
| BSA aqueous solution | 2.9 ± 0.5 | −19.71 |
| OVA aqueous solution | 2.5 ± 0.5 | −15.51 |

Comparative Examples 1 to 3

Preparation of Dispersion Solution of Complex of Cerium Oxide Nanoparticle with BSA To 1 mL of 5% by mass of BSA aqueous solution was added each of 1 μL (mass ratio BSA/CeO₂=25; Comparative Example 1), 10 μL (mass ratio BSA/CeO₂=2.5; Comparative Example 2), and 100 μL (mass ratio BSA/CeO₂=0.25; Comparative Example 3) of 20% by mass of commercially available nanoceria aqueous solution. Then, the resulting mixture was allowed to statically leave for 2 hours at room temperature. After the reaction was completed, the reaction solution was concentrated and purified using a 30 kD ultrafiltration membrane. Then, after this was added with 25-mM HEPES buffer solution (pH 7) to make the volume thereof to 1 mL, the hydrodynamic diameter and zeta potential thereof were measured. The results are listed in Table 2.

The results indicate that the hydrodynamic diameters indicated by the dispersion solutions prepared by simply mixing the cerium oxide nanoparticle with BSA were significantly increased compared to that indicated by the BSA solution. The zeta potentials of the prepared dispersion solutions were found to be far outside the range of −15 mV to +15 mV of the zeta potential of the BSA solution at pH 7.

TABLE 2

| Sample | Hydrodynamic diameter [nm] | Zeta potential [mV] |
|---|---|---|
| Comparative Example 1 (BSA/CeO2 mixing ratio = 25) | 818 ± 211 | −27.83 |
| Comparative Example 2 (BSA/CeO2 mixing ratio = 2.5) | 174 ± 115 | +30.82 |
| Comparative Example 3 (BSA/CeO2 mixing ratio = 0.25) | 9.3 ± 1.8 | +43.54 |

Examples 1 to 4

Preparation of Dispersion Solution of Complex of Cerium Oxide Nanoparticle with BSA To 10 mL of 5% by mass of BSA aqueous solution in each of the four glass test tubes was added each of 100 μL (mass ratio BSA/Ce(NO₃)₃×6H₂O=5; Example 1), 200 μL (mass ratio BSA/Ce(NO₃)₃×6H₂O=2.5; Example 2), 400 μL (mass ratio BSA/Ce(NO₃)₃×6H₂O=1.25; Example 3), and 800 μL (mass ratio BSA/Ce(NO₃)₃×6H₂O=0.625; Example 4) of 10% by mass of the commercially available cerium (III) nitrate hexahydrate aqueous solution. To each test tube, 100 μL, 200 μL, 400 μL, and 800 μL of 1.2% by mass of aqueous hydrogen peroxide solutions each were added. Then, they were stirred at room temperature for 1 hour to obtain yellow dispersion solutions. The dispersion solution was concentrated and purified using a 30 kD ultrafiltration membrane. Then, after 25 mM HEPES buffer solution (pH 7) was added to make the volume thereof to 1 mL, the hydrodynamic diameter and zeta potential thereof were measured. The results are listed in Table 3.

The results indicate that the hydrodynamic diameters indicated by the above-prepared dispersion solutions of the complex of cerium oxide nanoparticle with BSA were 10 times or less compared to the hydrodynamic diameter indicated by the BSA solution (Reference Example 1, Table 1). The zeta potentials of the prepared dispersion solutions of the complex were found to be in the range of −15 mV to +15 mV of the zeta potential of the BSA solution at pH 7.

TABLE 3

|  | Hydrodynamic diameter [nm] | Zeta potential [mV] | Catalase activity [U/mL] |
|---|---|---|---|
| Example 1 | 9.1 ± 1.7 | −19.60 | 1.6 |
| Example 2 | 10.7 ± 1.8 | −20.05 | 1.3 |
| Example 3 | 10.9 ± 1.9 | −22.52 | 1.2 |
| Example 4 | 12.2 ± 2.1 | −21.26 | 1.2 |

Catalase Activity Measurement of Dispersion Solutions of Examples 1 to 4

The catalase activity of each dispersion solution prepared as described above was measured.

The catalase activity was measured by using AmplexRed Catalase Assay Kit (A22180) manufactured by Thermo Fisher Scientific Inc. in accordance with the protocol. To describe simply, 50 μL of Reaction Buffer, 25 μL each of the dispersion solutions that had been prepared in Examples 1 to 4 having the concentration of 400 μg/mL, and 25 μL of the aqueous 40 μM hydrogen peroxide solution were mixed; then, the resulting mixture was allowed to statically leave for 30 minutes to carry out the decomposition reaction of hydrogen peroxide. The reaction solution was passed through a 30 kD ultrafiltration membrane. Then, 100 μL of the flow-through solution was mixed with 50 μL of Working Solution to carry out the reaction at 37° C. for 30 minutes. The resorufin generated by the reaction was excited at 544 nm, and the fluorescence intensity at 590 nm was measured. By comparing with the calibration curve prepared by the catalase standard whose activity value had already been known, the catalase activity of each of the dispersion solutions was calculated. The results are listed in Table 3.

From these results, we confirmed that the dispersion solutions prepared in Examples 1 to 4 had high catalase activity.

Examples 5 to 8

Preparation of Dispersion Solution of Complex of Cerium Oxide Nanoparticle with OVA The BSA protein used in Examples 1 to 4 was changed to OVA, and the use amounts of cerium (III) nitrate hexahydrate and of hydrogen peroxide were changed as appropriate to obtain the dispersion solutions of the complex with OVA.

To 10 mL of 5% by mass of OVA aqueous solution in each of the four glass test tubes was added each of 25 μL (mass ratio OVA/Ce(NO₃)₃×6H₂O=20; Example 5), 50 μL (mass ratio OVA/Ce(NO₃)₃×6H₂O=10; Example 6), 100 μL (mass ratio OVA/Ce(NO₃)₃×6H₂O=5; Example 7), and 200 μL (mass ratio OVA/Ce(NO₃)₃×6H₂O=2.5; Example 8) of 10% by mass of commercially available cerium (III) nitrate hexahydrate aqueous solution. To each test tube, 25 μL, 50 μL, 100 μL, and 200 μL of 1.2% by mass of aqueous hydrogen peroxide solutions each were added. Then, they were stirred at room temperature for 1 hour to obtain yellow dispersion solutions. The dispersion solution was concentrated and purified using a 30 kD ultrafiltration membrane. Then, after 25 mM HEPES buffer solution (pH 7) was added to make the volume thereof to 1 mL, the hydrodynamic diameter and zeta potential thereof were measured. The results are listed in Table 4.

The results indicate that the hydrodynamic diameters indicated by the above-prepared dispersion solutions of the complex of cerium oxide nanoparticle with OVA were 10 times or less compared to the hydrodynamic diameter indicated by the OVA solution (Reference Example 1, Table 1). The zeta potentials of the prepared dispersion solutions of the complex were found to be in the range of −15 mV to +15 mV of the zeta potential of the OVA solution at pH 7.

TABLE 4

|  | Hydrodynamic diameter [nm] | Zeta potential [mV] | Catalase activity [U/ml] |
|---|---|---|---|
| Example 5 | 10.5 ± 1.4 | −22.00 | 1.4 |
| Example 6 | 4.0 ± 0.8 | −15.67 | 1.6 |
| Example 7 | 5.5 ± 1.0 | −17.35 | 1.3 |
| Example 8 | 6.0 ± 1.4 | −6.43 | 1.2 |

Catalase Activity Measurement of Dispersion Solutions of Examples 5 to 8

The catalase activity of each dispersion solution prepared as described above was measured in the same way as in Examples 1 to 4. The results are listed in Table 4.

From these results, we confirmed that the dispersion solutions prepared in Examples 5 to 8 had high catalase activity.

Reference Example 2

Measurement of Hydrodynamic Diameter and Zeta Potential of IgG Aqueous Solution

As in Reference Example 1, IgG was dissolved in 25 mM HEPES buffer solution (pH 7). Then, the hydrodynamic diameter and zeta potential thereof were measured. The results are listed in Table 5.

TABLE 5

| Sample | Hydrodynamic diameter [nm] | Zeta potential [mV] |
|---|---|---|
| IgG Aqueous solution | 11.1 ± 1.6 nm | −11.56 |

Examples 9 to 12

Preparation of Dispersion Solution of the Complex of Cerium Oxide Nanoparticle with IgG The BSA protein used in Examples 1 to 4 was changed to IgG, and the use amounts of cerium (III) nitrate hexahydrate and hydrogen peroxide were changed as appropriate to obtain the dispersion solutions of the complex with IgG.

To 10 mL of 5% by mass of IgG aqueous solution in each of the four glass test tubes was added each of 25 μL (mass ratio IgG/Ce(NO₃)₃×6H₂O=20; Example 9), 50 μL (mass ratio IgG/Ce(NO₃)₃×6H₂O=10; Example 10), 100 μL (mass ratio IgG/Ce(NO₃)₃×6H₂O=5; Example 11), and 200 μL (mass ratio IgG/Ce(NO₃)₃×6H₂O=2.5; Example 12) of 10% by mass of commercially available cerium (III) nitrate hexahydrate aqueous solution. To each test tube, 25 μL, 50 μL, 100 μL, and 200 μL of 1.2% by mass of aqueous hydrogen peroxide solutions each were added. Then, they were stirred at room temperature for 1 hour to obtain yellow dispersion solutions. The dispersion solution was concentrated and purified using a 30 kD ultrafiltration membrane. Then, after 25 mM HEPES buffer solution (pH 7) was added to make the volume thereof to 1 mL, the hydrodynamic diameter and zeta potential thereof were measured. The results are listed in Table 6.

The results indicate that the hydrodynamic diameters indicated by the above-prepared dispersion solutions of the complex of cerium oxide nanoparticle with IgG were 10 times or less compared to the hydrodynamic diameter indicated by the IgG solution (Reference Example 2, Table 5).

The zeta potentials of the prepared dispersion solutions of the complex were found to be in the range of −15 mV to +15 mV of the zeta potential of the IgG solution at pH 7.

TABLE 6

|  | Hydrodynamic diameter [nm] | Zeta potential [mV] | Catalase activity [U/ml] |
|---|---|---|---|
| Example 9 | 19.9 ± 7.4 | −12.78 | 1.3 |
| Example 10 | 28.3 ± 8.8 | −14.68 | 1.4 |
| Example 11 | 31.4 ± 9.2 | −13.35 | 1.2 |
| Example 12 | 40.1 ± 13.5 | −5.33 | 1.2 |

Catalase Activity Measurement of Dispersion Solutions of Examples 9 to 12

The catalase activity of each dispersion solution prepared as described above was measured in the same way as in Examples 1 to 4. The results are listed in Table 6.

From these results, we confirmed that the dispersion solutions prepared in Examples 9 to 12 had high catalase activity.

The invention claimed is:

1. A method of producing a dispersion solution of a complex of cerium oxide nanoparticle with protein, the method comprising:

mixing a solution containing the protein with a solution containing a cerium (III) ion or with a cerium (III) salt; and adding an oxidizing agent thereto to produce a dispersion solution of a complex of cerium oxide nanoparticles with protein, the oxidizing agent oxidizing a cerium (III) ion to cerium (IV), and the cerium oxide nanoparticles consisting of a mixture of $Ce_2O_3$ and $CeO_2$, wherein the oxidizing agent is selected from the group consisting of nitric acid, potassium nitrate, hypochlorous acid, chlorous acid, chloric acid, perchloric acid, halogens, permanganate salts, chromic acid, dichromic acid, sulfuric acid, or hydrogen peroxide.

2. The method according to claim 1, wherein a molecular weight of the protein is 5 kD to 200 kD.

3. The method according to claim 1, wherein the protein is a protein present in blood.

4. The method according to claim 1, wherein the protein is albumin or globulin.

5. The method according to claim 1, wherein an addition amount of the oxidizing agent relative to the cerium (III) ion as a molar equivalent is 0.1 to 10.

* * * * *